(12) United States Patent
Karl et al.

(10) Patent No.: US 10,717,702 B2
(45) Date of Patent: Jul. 21, 2020

(54) POLYASPARTIC ESTER COMPOSITIONS, AND METHODS OF MAKING AND USING SAME

(71) Applicant: CARGILL, INCORPORATED, Wayzata, MN (US)

(72) Inventors: Andrew M. Karl, Maple Grove, MN (US); Todd L. Kurth, Maple Grove, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/489,556

(22) PCT Filed: Mar. 2, 2018

(86) PCT No.: PCT/US2018/020604
§ 371 (c)(1),
(2) Date: Aug. 28, 2019

(87) PCT Pub. No.: WO2018/160932
PCT Pub. Date: Sep. 7, 2018

(65) Prior Publication Data
US 2020/0010405 A1    Jan. 9, 2020

Related U.S. Application Data

(60) Provisional application No. 62/466,894, filed on Mar. 3, 2017.

(51) Int. Cl.
*C07C 229/48* (2006.01)
*C07C 227/18* (2006.01)

(52) U.S. Cl.
CPC .......... *C07C 229/48* (2013.01); *C07C 227/18* (2013.01)

(58) Field of Classification Search
CPC .......................... C07C 229/48; C07C 227/18
USPC ......................................................... 560/118
See application file for complete search history.

(56) References Cited

U.S. PATENT DOCUMENTS

| 2007/0078255 A1* | 4/2007 | Mager .................... C08G 18/10 528/59 |
| 2016/0024339 A1* | 1/2016 | Squiller ............... C09D 175/02 524/589 |

FOREIGN PATENT DOCUMENTS

| WO | 2015120941 A1 | 8/2015 |
| WO | WO-2015120941 A1 * | 8/2015 ............. C08G 18/73 |

OTHER PUBLICATIONS

Angeloff, et al.", Two-Component Aliphatic Polyurea Coatings for High Productivity Applications", JPCL, pp. 42-47, 2002.*
Angeloff, C., et al., "Two-Component Aliphatic Polyurea Coatings for High Productivity Applications", JPCL Aug. 2002, pp. 42-47.

* cited by examiner

*Primary Examiner* — Deborah D Carr

(57) ABSTRACT

Methods of preparing a polyaspartic ester composition comprise reacting a primary diamine reactant composition with a diester reactant composition under conditions to prepare a polyaspartic ester composition having a primary amine value of less than 35 mg KOH/g wherein, at the time of the reaction, the combined water content of the primary diamine reactant composition and the diester reactant composition is less than 300 ppm. Compositions and methods of use of the compositions are also described.

19 Claims, 3 Drawing Sheets

POLYASPARTIC ESTER COMPOSITIONS, AND METHODS OF MAKING AND USING SAME

CROSS REFERENCE TO RELATED APPLICATIONS

This application is a national phase application of International Application No. PCT/US2018/020604, filed Mar. 2, 2018, entitled POLYASPARTIC ESTER COMPOSITIONS, AND METHODS OF MAKING AND USING SAME, which claims the benefit of U.S. Provisional Patent Application No. 62/466,894, filed Mar. 3, 2017, entitled POLYASPARTIC ESTER COMPOSITIONS, AND METHODS OF MAKING AND USING SAME, each of which is hereby incorporated by reference in its entirety.

FIELD

The present invention relates to methods of making polyaspartic ester compositions, the compositions themselves, and methods of using the compositions.

BACKGROUND

Two-component polyurea coating compositions containing a polyisocyanate in combination with a polyaspartic ester component are known. They are suitable for the formation of coatings and can be adjusted to produce coatings that are hard, elastic, abrasion resistant, solvent resistant, and especially weather resistant.

U.S. Pat. No. 5,126,170 discloses a process for making polyurethane coatings in which an isocyanate-reactive component b) includes a polyaspartic ester mixture made from an optionally-substituted maleic or fumaric acid ester and a primary amine. U.S. Pat. No. 6,458,293 discloses a method for making an asymmetric polyaspartic ester mixture by sequentially (a) forming an ester mixture containing a dimethyl-substituted first ester component and a second ester component substituted with an alkyl group having at least two carbon atoms and (b) reacting the ester component with an amine component, such that the equivalent number ratio of the first ester component and the second ester component is sufficient to prevent the formation of a reaction-stopping crude mixture containing dimethyl fumarate crystals. US Patent Application Publication No. 2005/0075477 describes a process for preparing aspartates.

SUMMARY

Polyurea coating compositions are prepared by reacting isocyanate with an amine. Due to the reactive nature of isocyanates, the nature of the amine has a substantial impact on the speed of reaction to form the polyurea coating. For this reason, polyaspartic esters have been prepared that provide a hindered secondary amine, which in turn leads to an isocyanate/amine reactive mixture having a suitable Gel Time for effective application of the reactive mixture to a substrate.

Polyaspartic esters are prepared by reacting a primary amine with maleic or fumaric acid esters in an "aza"—Michael addition reaction, as shown in Formula 1.

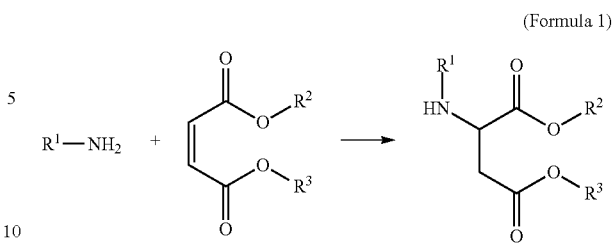

(Formula 1)

An example of such a polyaspartic ester is Cargill's Polyaspartic Ester 201 (also known as "Altor 201"), which has the chemical structure of Formula 2.

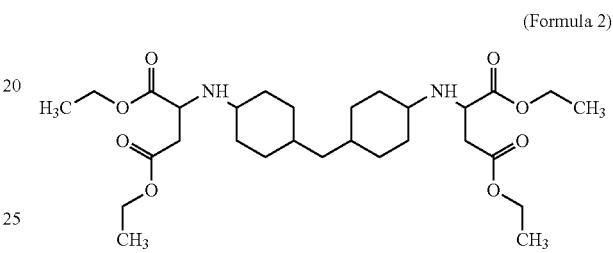

(Formula 2)

The Polyaspartic Ester 201 composition is an exceptional starting material for preparation of polyurea compositions, and in particular polyurea coatings, when reacted with polyisocyanates. However, the Gel Time of the reaction mixture of the 201 polyaspartic ester with polyisocyanates is shorter than desirable in certain applications. It is possible to prepare polyaspartic esters having a longer reaction mixture Gel Time by modifying the chemical structure to further hinder the compound. For example, a polyaspartic ester of Formula 3 provides a greatly extended Gel Time (i.e. approx. 8 hours).

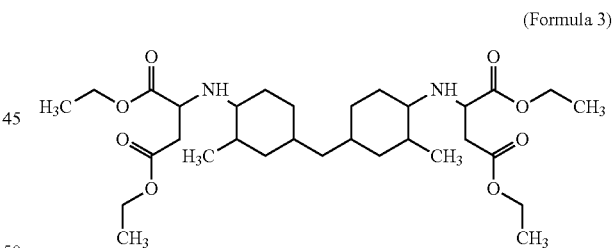

(Formula 3)

However, this chemical structure modification can lead to drawbacks, in that such resulting polyurea compositions exhibit a long dry-through time (e.g. about 24 hours) and do not have the same coating performance properties as those made from the more quick setting polyaspartic compositions.

Simply blending fast-curing and slow-curing polyaspartic acid compositions does not provide a final product that exhibits a proportional improvement in properties. Rather, final polyurea coatings prepared from such blends have been found to exhibit more of the properties of the slower curing polyaspartic acid component, even when the faster curing polyaspartic acid component is present in excess.

It has surprisingly been found that careful control of the water content of the diamine and diester starting material reactant compositions used to prepare the polyaspartic ester composition provides polyaspartic ester compositions exhibiting excellent Gel Time and other physical properties that are not achieved by compositions prepared without water content control of starting material reactant compositions.

In an aspect, a method of preparing a polyaspartic ester composition comprises
  a) providing a primary diamine reactant composition;
  b) providing a diester reactant composition comprising a diester selected from the group consisting of diesters of maleic acid, fumaric acid or combinations thereof; and
  c) reacting the primary diamine reactant composition with the diester reactant composition under conditions to prepare a polyaspartic ester composition having a primary amine value of less than 35 mg KOH/g;
  wherein, at the time of the reaction, the combined water content of the primary diamine reactant composition and the diester reactant composition is less than 300 ppm.

In an aspect, a method of preparing a polyaspartic ester composition comprises
  a) providing primary diamine reactant composition comprising at least one diamine compound;
  b) providing a diester reactant composition comprising at least one diester compound selected from the group consisting of diesters of maleic acid, fumaric acid or combinations thereof; and
  c) reacting the primary diamine reactant composition with the diester reactant composition under conditions to prepare a polyaspartic ester composition having a primary amine value of less than 35 mg KOH/g;
  wherein, at the time of the reaction, the combined water content of the primary diamine reactant composition and the diester reactant composition is less than 300 ppm; and
  wherein the diamine compounds and the diester compounds of the primary diamine reactant composition and the diester reactant composition are selected such that the polyaspartic ester composition, when reacted with hexamethylene diisocyanate trimer, has a Gel Time of from about 40 minutes to about 100 minutes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this application, illustrate several aspects of the invention and together with a description of the embodiments serve to explain the principles of the invention. A brief description of the drawings is as follows.

DETAILED DESCRIPTION

Figure 1:
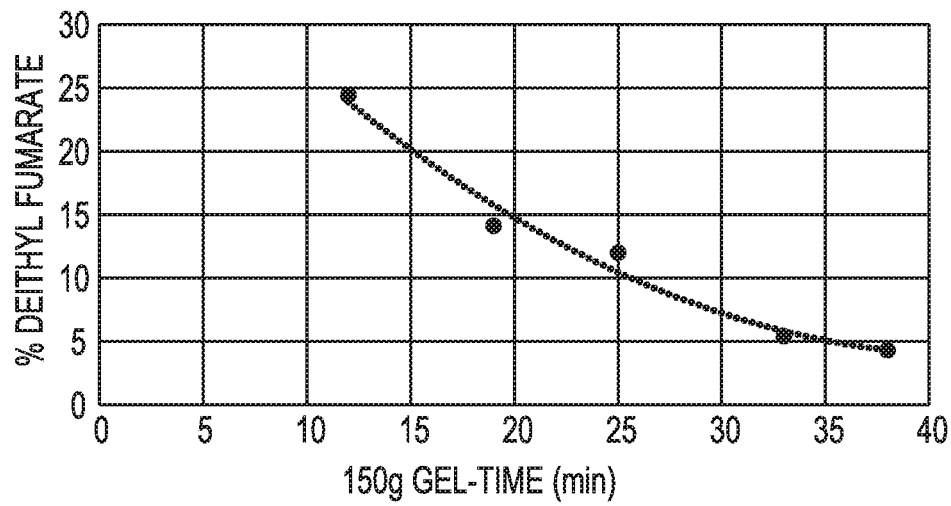
FIG. 1 is a graph showing the relationship of DEF vs. 150 g gel time for high moisture HMDA added to High moisture DEM.

The aspects of the present invention described below are not intended to be exhaustive or to limit the invention to the precise forms disclosed in the following detailed description. Rather a purpose of the aspects chosen and described is by way of illustration or example, so that the appreciation and understanding by others skilled in the art of the general principles and practices of the present invention can be facilitated.

In an aspect, the diamine compounds and the diester compounds of the primary diamine reactant composition and the diester reactant composition are selected such that the polyaspartic ester composition has a Gel Time of from about 45 minutes to about 90 minutes, or from about 55 minutes to about 80 minutes, or from about 60 minutes to about 75 minutes.

In an aspect, at the time of the reaction, the combined water content of the primary diamine reactant composition and the diester reactant composition is less than 200 ppm, or less than 100 ppm, or less than 75 ppm, or less than 50 ppm, or less than 25 ppm. In an aspect, at the time of the reaction, the combined water content of the primary diamine reactant composition and the diester reactant composition as noted above is additionally is greater than 1 ppm, or greater than 5 ppm, or greater than 10 ppm, or greater than 15 ppm.

It has been found that free primary amines are much more reactive than hindered secondary amines, and that the presence of substantial amounts of free (i.e. unreacted) primary amines undesirably shortens Gel Time and adversely affects other properties of the ultimate polyurea compositions as well. In an aspect, the primary diamine reactant composition is reacted with the diester reactant composition under conditions to prepare a polyaspartic ester composition having a primary amine value of less than 20 mg KOH/g, or less than 15 mg KOH/g, or less than 10 mg KOH/g, or less than 5 mg KOH/g, or less than 1 mg KOH/g. In an aspect, the primary diamine reactant composition comprises a diamine wherein the amino groups are attached to aliphatic, cycloaliphatic, araliphatic and/or aromatic carbon atoms. In an aspect, the primary diamine reactant composition comprises a diamine is selected from a hindered diamine, an asymmetric diamine, a symmetric diamine, and a chiral diamine. In an aspect, the primary diamine reactant composition may additionally comprise polyamines, and in particular triamines. Examples of such diamines are disclosed in, e.g., U.S. Pat. Nos. 5,126,170; 6,458,293; and US Patent Application Publication No. 2005/0075477, the disclosures of which are incorporated herein by reference.

In an aspect, the primary diamine reactant composition comprises a diamine that is a methylene bis cyclohexylamine. In an aspect, the primary diamine reactant composition comprises a diamine that is 2,4'-methylene bis cyclohexylamine. In an aspect, from about 2 to 90 percent of the amine in the primary diamine reactant composition is 2,4'-methylene bis cyclohexylamine. It has been found that incorporating 2,4'-methylene bis cyclohexylamine in the primary diamine reactant composition provides a composition that exhibits increased gel time as compared to like methylene bis cyclohexylamine-containing compositions that do not incorporate 2,4'-methylene bis cyclohexylamine. In an aspect, from about 2 to 50 percent of the amine in the primary diamine reactant composition is 2,4'-methylene bis cyclohexylamine. In an aspect, from about 2 to 30 percent of the amine in the primary diamine reactant composition is 2,4'-methylene bis cyclohexylamine. In an aspect, from about 2 to 20 percent of the amine in the primary diamine reactant composition is 2,4'-methylene bis cyclohexylamine. In an aspect, from about 5 to 30 percent of the amine in the primary diamine reactant composition is 2,4'-methylene bis cyclohexylamine. In an aspect, from about 2 to 10 percent of the amine in the primary diamine reactant composition is 2,4'-methylene bis cyclohexylamine. In an aspect, from about 2 to 5 percent of the amine in the primary diamine reactant composition is 2,4'-methylene bis cyclohexylamine. In an aspect, the primary diamine reactant composition comprises a diamine that is 4,4'-methylene bis cyclohexylamine ("HMDA"—also known as bis p-aminocyclohexyl methane or "PACM"). In an aspect, at least about 80 percent of the amine in the primary diamine reactant composition is 4,4'-methylene bis cyclohexylamine. In an aspect, at least about 90 percent of the amine in the primary diamine reactant composition is 4,4'-methylene bis cyclohexylamine. In an aspect, all of the amine in the primary diamine reactant composition is 4,4'-methylene bis cyclohexylamine. In an aspect, the primary diamine reactant composition comprises a mixture of two diamines that are 2,4'-methylene bis cyclohexylamine and 4,4'-methylene bis cyclohexylamine.

In an aspect, the diester reactant composition comprising a diester selected from diesters of maleic acid. In an aspect, the diester is selected from mixtures of diesters of maleic acid. In an aspect, the diester is selected from C1-4 alkyl diesters of maleic acid, or mixtures thereof.

In an aspect, the diester is diethyl maleate.

As noted above, at the time of the reaction, the combined water content of the primary diamine reactant composition and the diester reactant composition is less than 300 ppm. In an aspect, the combined water content of the primary diamine reactant composition and the diester reactant composition is less than 200 ppm, or less than 100 ppm, or less than 75 ppm, or less than 50 ppm, or less than 25 ppm. In an aspect, the combined water content of the primary diamine reactant composition and the diester reactant composition is greater than 1 ppm, or greater than 5 ppm, or greater than 10 ppm, or greater than 15 ppm.

In an aspect, the water content of each of the primary diamine reactant composition and the diester reactant composition is reduced separately, prior to mixing, by an appropriate technique. When the water content of each of the primary diamine reactant composition and the diester reactant composition is reduced separately, the water content of the reactant compositions may be the same or different from each other, provided that the combination of the water contents is below the indicated maximum permitted amount. For example, in an aspect, the water content of the primary diamine reactant composition could be 25 ppm, while the water content of the diester reactant composition is 35 ppm.

In an aspect, the primary diamine reactant composition and the diester reactant composition are mixed together, and then just prior to the reaction of the diamine with the diester, the water content of the combined composition is reduced by an appropriate technique.

The primary diamine reactant composition and the diester reactant composition may be prepared on site or acquired from a third party supplier. It should be noted that such compositions are hygroscopic in nature, so that even when supplied at a low water content, careful handling of the composition is required to provide the composition at the desired low water content at the time of reaction.

The water content of the primary diamine reactant composition and the diester reactant composition or mixtures thereof may be reduced by any appropriate technique now apparent to the skilled artisan. In an aspect, water content may be reduced by subsurface sparge with an inert gas in combination with vacuum at elevated temperature. In an aspect, the water content may be reduced by nitrogen sparge in conjunction with a vacuum at from about 10 to 40 torr at a temperature of from about 50 to 90° C. In an aspect, water content may be reduced by a wiped film evaporator (WFE).

The polyaspartic ester compositions made by the methods described herein exhibit unique properties, for example as an intermediate in various reactions. In an aspect, the polyaspartic ester composition is provided as a 100% solids composition.

In an aspect, the present polyaspartic ester compositions are useful in preparing excellent polyureas by reaction of the polyaspartic ester composition with at least one polyisocyanate compound. In an aspect, the polyurea is provided in the form of a coating having a thickness of from 2 to 20 mils.

Physical Property Definitions

For purposes of the present invention, all physical property characteristics described herein of the polyaspartic ester composition are determined using a composition of a polyaspartic ester/hexamethylene diisocyanate trimer composition (or the final polyurea formed by this composition) that is formed by mixing the polyaspartic ester composition to be tested (in the form of a 100% solids composition) with a 100% solids hexamethylene diisocyanate trimer composition at a 60/40% weight ratio (+/−1%). Unless otherwise indicated, all tests are carried out in a Standard Environment as defined in ASTM D3924-80 (i.e. an enclosed environmental chamber set at 24° C. and 50% RH), and all test panels as necessary for tests are prepared as set forth in ASTM D609-00 on a linear dry time recorder using a dry film thickness of 6 mils.

For purposes of the present invention, "Gel Time" is defined as the amount of time it takes for an initial mixed viscosity of a polyaspartic ester/hexamethylene diisocyanate trimer composition to become stringy, or gel-like, though not quite fully cured, as more completely described in as defined in ASTM D2471-99. Timing of this test starts from the moment the product is mixed, and is measured at room temperature (23° C.). In an aspect, the Gel Time of the polyaspartic ester composition is from about 40 minutes to about 100 minutes.

In an aspect, the diamine compounds and the diester compounds of the primary diamine reactant composition and the diester reactant composition are selected such that the polyaspartic ester composition has a Gel Time of from about 40 minutes to about 80 minutes. In an aspect, the diamine compounds and the diester compounds of the primary diamine reactant composition and the diester reactant composition are selected such that the polyaspartic ester composition has a Gel Time of from about 50 minutes to about 70 minutes. In an aspect, the diamine compounds and the diester compounds of the primary diamine reactant composition and the diester reactant composition are selected such that the polyaspartic ester composition has a Gel Time of from about 60 minutes to about 70 minutes.

For purposes of the present invention, the Primary Amine Value as defined in AOCS Method Ta 3a-64.

For purposes of the present invention, the Shore D Hardness test is carried out as set forth in ASTM D2240-00, in an enclosed environmental chamber set to 24° C. and 50% RH using 15 grams of material.

In an aspect, the diamine compounds and the diester compounds of the primary diamine reactant composition and the diester reactant composition are selected such that the polyaspartic ester composition, when reacted with hexamethylene diisocyanate trimer as noted above, has a Shore D Hardness at 24 hours of greater than 60, or has a Shore D hardness at 24 hours of from 70 to 100.

For purposes of the present invention, the 15 second Small Cracking Mandrel Bend is carried out as set forth in ASTM D522-93a, conducted on 0.8 mm cold rolled steel panels. Each panel was coated and allowed to cure for a period of 7 days. Each test was conducted in triplicate using a film thickness of 10 mils.

In an aspect, the diamine compounds and the diester compounds of the primary diamine reactant composition and the diester reactant composition are selected such that the polyaspartic ester composition, when reacted with hexamethylene diisocyanate trimer as noted above, has a 15 second Small Cracking Mandrel Bend value of greater than 10% elongation.

For purposes of the present invention, Chemical Resistance rating is carried out using the procedure of the MEK double rub test set forth in ASTM D4752-03. All testing was conducted on 0.8 mm cold rolled steel panels. The panels were coated at 10 mils DFT and allowed to cure for 7 days at 24° C. and 50% RH.

In an aspect, the diamine compounds and the diester compounds of the primary diamine reactant composition and the diester reactant composition are selected such that the polyaspartic ester composition, when reacted with hexamethylene diisocyanate trimer as noted above, has a Chemical Resistance rating at 250 rubs of at least 4 for methyl ethyl ketone, or has a Chemical Resistance rating at 250 rubs of at least 5 for methyl ethyl ketone.

In an aspect, the diamine compounds and the diester compounds of the primary diamine reactant composition and the diester reactant composition are selected such that the polyaspartic ester composition, when reacted with hexamethylene diisocyanate trimer as noted above, has a Chemical Resistance rating at 250 rubs of at least 4 for Skydrol, or has a Chemical Resistance rating at 250 rubs of at least 5 for Skydrol.

For purposes of the present invention, Impact Resistance Test rating is carried out using the procedure set forth in ASTM D2794-93. All testing was conducted using 0.63 mm steel panels. The panels were coated with 10 mils of dry film thickness and allowed to cure at 24 C and 50% RH for 7 days. Apart from visual observations, $CuSO_4$ was used to determine the breaks in the film as the solution causing iron-rusting upon contact with the steel substrate.

In an aspect, the diamine compounds and the diester compounds of the primary diamine reactant composition and the diester reactant composition are selected such that the polyaspartic ester composition, when reacted with hexamethylene diisocyanate trimer as noted above, has an Impact Resistance Test Failure of greater than 30 lbs.

For purposes of the present invention, Buchholz Hardness Mar Resistance is carried out using the procedure set forth in ISO 2815. Each test was conducted of 0.8 mm cold rolled steel panels and coated with 5 mils of material. The panels were allowed to cure for 7 days at 24° C. at 50% RH.

In an aspect, the diamine compounds and the diester compounds of the primary diamine reactant composition and the diester reactant composition are selected such that the polyaspartic ester composition, when reacted with hexamethylene diisocyanate trimer as noted above, has a Buchholz Hardness Mar Resistance of greater than 85.

The following acronyms are used in the present examples:
DEM=Diethyl maleic acid ester
DEF=Diethyl fumaric acid ester
HMDA=4,4'-methylenebiscyclohexylamine
WFE=Wiped Film Evaporator

EXAMPLES

Comparative Example A—Attempted Drying of Polyaspartic Ester Composition after Reaction of a Primary Diamine Reactant Composition with a Diester Reactant Composition Polyaspartic ester compositions were prepared by addition of High Moisture HMDA (550 ppm water) to High Moisture DEM (612 ppm water) and sparging with nitrogen at a rate of 0.0328 cu ft/hr Nitrogen and applying a vacuum of 50 torr and relief 3 times in a 2 L reactor. This reaction was conducted in two separate batches in a clean Parr reactor. Both reactors were degassed to remove both dissolved and ambient air.

In the first batch, HMDA was added to the DEM via a clear transfer tube over a period of 1.3 hrs. This reaction was brought down to 4.3% free DEF and the corresponding polyurea formed from this polyaspartic ester composition had a gel-time of 38 minutes.

A portion of this first batch of the above prepared polyaspartic ester composition was loaded into a sealed Parr reactor and dried under 50 torr vacuum and 0.0328 cu ft/hr Nitrogen-80° C.—2 L reactor to 46 ppm.

The gel-time of the corresponding polyurea formed from this dried polyaspartic ester composition was 41 minutes.

Thus, there was no dramatic increase in the gel time from drying a final material that has a short gel time. As shown from batch one above, that material was fairly wet (585 ppm) and only resulted with a 38 min gel-time with a high level of conversion (3.8% DEF). FIG. 1 is a graph showing the relationship of DEF vs. 150 g gel time for high moisture HMDA added to High moisture DEM.

DEF content is shown in the Figure because it has been found that there is a direct correlation between primary amine value and the % DEF in the composition. As such, it was elected to track the following reactions via % DEF. From this correlation, we can conclude the reaction rate of the amine is equal to that of the DEM (i.e., 1 DEM=1 amine equivalent).

Drying this material down to 46 ppm as detailed in batch two above only increased the gel-time by 3 minutes. As such, it does not appear to be possible to sufficiently increase gel time by simply drying a high moisture content polyaspartic ester composition. Additionally, attempting to dry high moisture content polyaspartic ester composition via a batch reactor using vacuum and elevated temperatures resulted in a large increase in color (84 APHA→2.3 Gardner).

Example 1—Preparation of and Use of a Polyaspartic Ester Composition from Dry Reactants Low moisture HMDA (38 ppm) added to low moisture DEM (45 ppm)—0.0655 cu-ft/hr $N_2$-Vacuum to 50 torr and relief 3 times to de-gas—2 L reactor.

Figure 2:
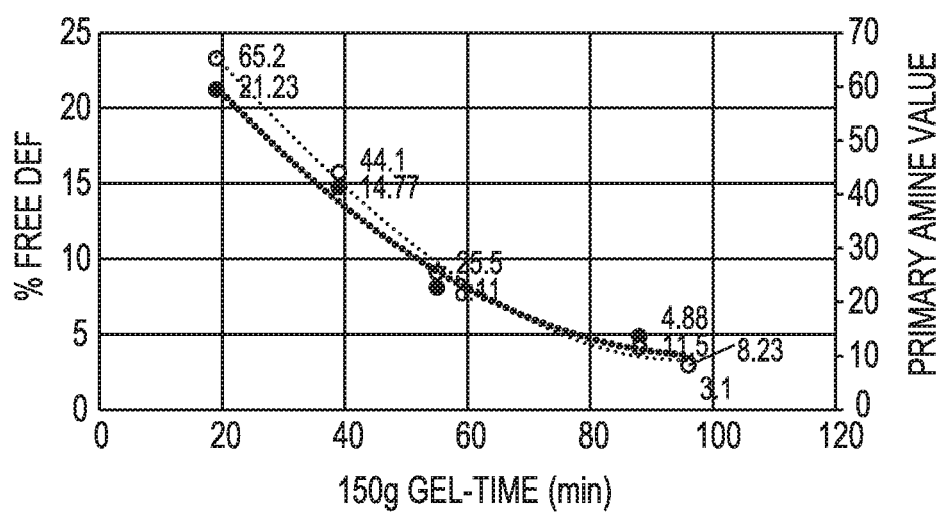
FIG. 2 is a graph showing reaction progression of a dry batch using degassed materials.

This reaction was conducted in a clean Parr reactor. Both reactors were degassed to remove both dissolved and ambient air. HMDA was added to the DEM via a clear transfer tube over a period of 1.5 hrs. This reaction was brought down to 3.1% free DEF and a corresponding gel-time of 93 minutes. FIG. 2 is a graph showing reaction progression of this dry batch using degassed materials. This reaction tracks both DEF and primary amine value.

Evaluation of Effect of Water Content and Isomers in Preparation of Polyaspartic Ester Composition Comparative Example B—Preparation and Evaluation of Polyaspartic Ester Composition Using High Moisture Content Reaction Materials and Predominantly DEF Isomer Starting Material High moisture HMDA (199 ppm) added to high moisture (212 ppm) diester (82% DEF, 18% DEM)—0.0328 cu-ft/hr—1 L reactor The reactor was evacuated and re-pressurized with nitrogen 3 times. High moisture HMDA was added via an addition funnel over 1.8 hours to high moisture DEM/DEF. The reaction was brought down to 3.98% DEF over the course of 54 hours @ 70° C. with a final gel-time of 56 minutes.

Example 2—Preparation and Evaluation of Polyaspartic Ester Composition Using Low Moisture Content Reaction Materials and Predominantly DEF Isomer Starting Material Low moisture (49.8 ppm) HMDA added to low moisture (34 ppm) diester (82% DEF, 18% DEM)—0.0328 cu-ft/hr—1 L reactor The reactor was evacuated and re-pressurized with nitrogen 3 times. High moisture HMDA was added via an addition funnel over 2 hours to high moisture DEM/DEF. The reaction was brought down to 4.13% DEF over the course of 54 hours @ 70° C. with a final gel-time of 77 minutes.

Example 3—Preparation and Evaluation of Polyaspartic Ester Composition Using Low Moisture Content Reaction Materials and Predominantly DEM Starting Material Low moisture HMDA (45.5 ppm) added to low moisture DEM (28.8 ppm)—0.0655 cu-ft/hr—2 L reactor The reactor was evacuated and re-pressurized with nitrogen 3 times. High moisture HMDA was added via an addition funnel over 2 hours to high moisture DEM/DEF. The reaction was brought down to 4.44% DEF over the course of 50.5 hours @ 70° C. with a final gel-time of 74.5 minutes.

Comparative Example C—Preparation and Evaluation of Polyaspartic Ester Composition Using High Moisture Content Reaction Materials and Predominantly DEM Starting Material High moisture HMDA (209.19 ppm) added to high moisture DEM (161.0 ppm)—0.0655 cu-ft/hr—2 L reactor The reactor was evacuated and re-pressurized with nitrogen 3 times. High moisture HMDA was added via an addition funnel over 1.5 hours to high moisture DEM/DEF. The reaction was brought down to 4.45% DEF over the course of 50.5 hours @ 70° C. with a final gel-time of 52 minutes.

The starting materials of Comparative Examples B and C and of Examples 2 and 3 all utilized the exact same lot of HMDA and DEM. All materials dried with a WFE. High moisture starting materials of Comparative Examples B and C were prepared by addition of water to the dried starting materials.

Figure 3:
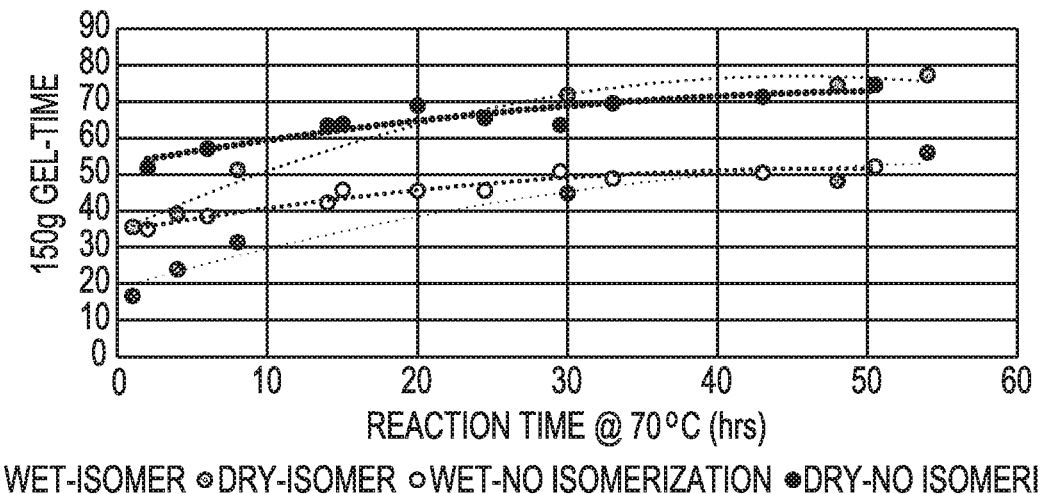
FIG. 3 is a graph showing Gel-Time progression of wet and dry batches.

FIG. 3 shows Gel-Time progression of wet and dry batches (i.e. Comparative Examples B and C, and Examples 2 and 3) with and without isomerization (i.e. predominantly DEF content). Non-isomerized DEM compositions react quickly.

Figure 4:
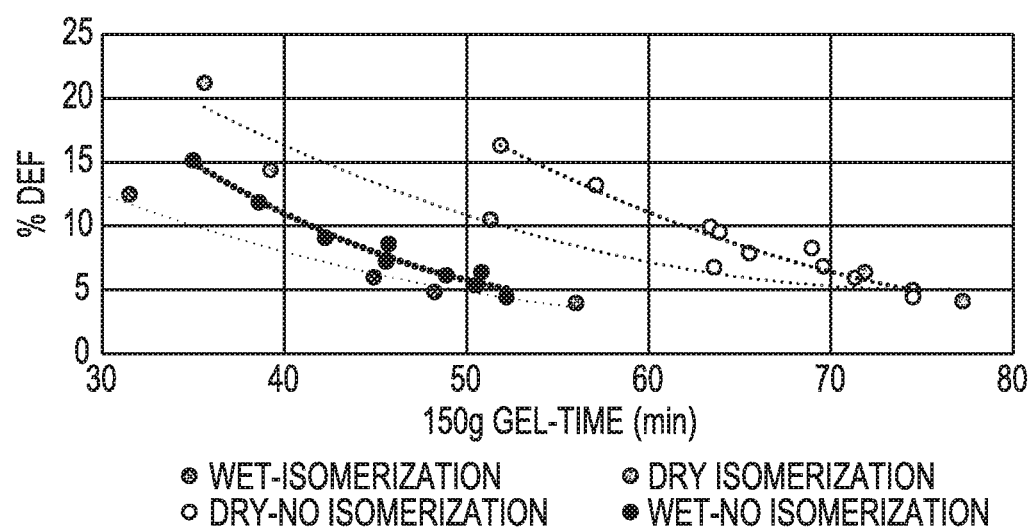
FIG. 4 is a graph showing Reaction progression via % DEF of wet and dry batches

FIG. 4 shows Reaction progression via % DEF of wet and dry batches (i.e.

Comparative Examples B and C, and Examples 2 and 3) with and without isomerization (i.e. predominantly DEF content). Non-isomerized DEM react compositions react quickly.

Figure 5:
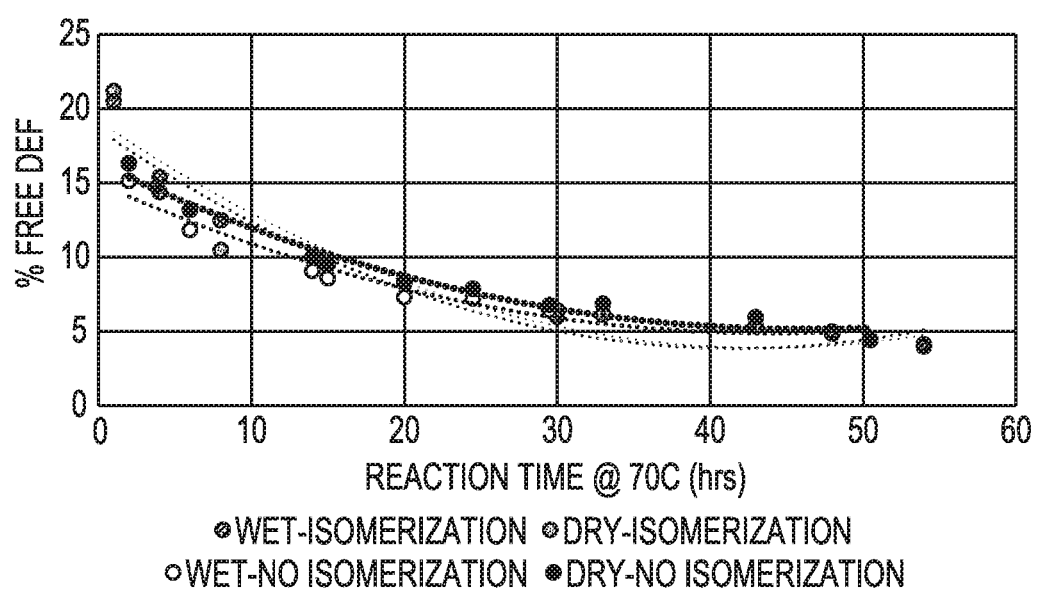
FIG. 5 is a graph showing DEF progression as a factor of reaction time for compositions.

FIG. 5 shows % DEF progression as a factor of reaction time for Comparative Examples B and C, and Examples 2 and 3. It is surprising that the kinetics are not greatly impacted, i.e. transition state energies do not seem to be altered.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise ratios. For example, "about" can mean greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values. Alternatively, particularly with respect to biological systems or processes, the term can mean within an order of magnitude, preferably within 5-fold, and more preferably within 2-fold, of a value.

Throughout this specification and claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein "consisting of" excludes any element, step, or ingredient not specified in the claim element. When used herein, "consisting essentially of" does not exclude materials or steps that do not materially affect the basic and novel characteristics of the claim. In the present disclosure of various embodiments, any of the terms "comprising", "consisting essentially of" and "consisting of" used in the description of an embodiment may be replaced with either of the other two terms.

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preparing a polyaspartic ester composition comprising
   a) providing a primary diamine reactant composition;
   b) providing a diester reactant composition comprising a diester selected from the group consisting of diesters of maleic acid, fumaric acid or combinations thereof, and
   c) reacting the primary diamine reactant composition with the diester reactant composition under conditions to prepare a polyaspartic ester composition having a primary amine value of less than 35 mg KOH/g;
   wherein, at the time of the reaction, the combined water content of the primary diamine reactant composition and the diester reactant composition is less than 300 ppm.

2. A method of preparing a polyaspartic ester composition comprising
   a) providing primary diamine reactant composition comprising at least one diamine compound;
   b) providing a diester reactant composition comprising at least one diester compound selected from the group consisting of diesters of maleic acid, fumaric acid or combinations thereof; and
   c) reacting the primary diamine reactant composition with the diester reactant composition under conditions to prepare a polyaspartic ester composition having a primary amine value of less than 35 mg KOH/g;
   wherein, at the time of the reaction, the combined water content of the primary diamine reactant composition and the diester reactant composition is less than 300 ppm; and
   wherein the diamine compounds and the diester compounds of the primary diamine reactant composition and the diester reactant composition are selected such that the polyaspartic ester composition, when reacted with hexamethylene diisocyanate trimer, has a Gel Time of from about 40 minutes to about 100 minutes.

3. The method of claim 2, wherein the diamine compounds and the diester compounds of the primary diamine reactant composition and the diester reactant composition are selected such that the polyaspartic ester composition, when reacted with hexamethylene diisocyanate trimer, has a Gel Time of from about 45 minutes to about 90 minutes, or from about 55 minutes to about 80 minutes, or from about 60 minutes to about 75 minutes.

4. The method of claim 2, wherein the diamine compounds and the diester compounds of the primary diamine reactant composition and the diester reactant composition are selected such that the polyaspartic ester composition, when reacted with hexamethylene diisocyanate trimer, has a Shore D Hardness at 24 hours of greater than 60.

5. The method of claim 2, wherein the diamine compounds and the diester compounds of the primary diamine reactant composition and the diester reactant composition are selected such that the polyaspartic ester composition, when reacted with hexamethylene diisocyanate trimer, has a Shore D hardness at 24 hours of from 70 to 100.

6. The method of claim 2, wherein the diamine compounds and the diester compounds of the primary diamine reactant composition and the diester reactant composition are selected such that the polyaspartic ester composition, when reacted with hexamethylene diisocyanate trimer, has a 15 second Small Cracking Mandrel Bend value of greater than 10.

7. The method of claim 2, wherein the diamine compounds and the diester compounds of the primary diamine reactant composition and the diester reactant composition are selected such that the polyaspartic ester composition, when reacted with hexamethylene diisocyanate trimer, has a Chemical Resistance rating at 250 rubs of at least 4 for methyl ethyl ketone, or has a Chemical Resistance rating at 250 rubs of at least 5 for methyl ethyl ketone.

8. The method of claim 2, wherein the diamine compounds and the diester compounds of the primary diamine reactant composition and the diester reactant composition are selected such that the polyaspartic ester composition, when reacted with hexamethylene diisocyanate trimer, has a Chemical Resistance rating at 250 rubs of at least 4 for Skydrol, or has a Chemical Resistance rating at 250 rubs of at least 5 for Skydrol.

9. The method of claim 2, wherein the diamine compounds and the diester compounds of the primary diamine reactant composition and the diester reactant composition are selected such that the polyaspartic ester composition, when reacted with hexamethylene diisocyanate trimer, has an Impact Resistance Test Failure of greater than 30 lbs.

10. The method of claim 2, wherein the diamine compounds and the diester compounds of the primary diamine reactant composition and the diester reactant composition are selected such that the polyaspartic ester composition, when reacted with hexamethylene diisocyanate trimer, has a Buchholz Hardness Mar Resistance of greater than 85.

11. The method of claim 1, wherein the primary diamine reactant composition comprises an amine that is 2,4'-methylene bis cyclohexylamine.

12. The method of claim 11, wherein from about 2 percent to about 20 percent of the amine in the primary diamine reactant composition is 2,4'-methylene bis cyclohexylamine.

13. The method of claim 1, wherein the primary diamine reactant composition comprises an amine that is 4,4'-methylene bis cyclohexylamine.

14. The method of claim 13, wherein at least about 80 percent of the amine in the primary diamine reactant composition is 4,4'-methylene bis cyclohexylamine.

15. The method of claim 13, wherein at least about 95 percent of the amine in the primary diamine reactant composition is 4,4'-methylene bis cyclohexylamine.

16. The method of claim 1, wherein the diester is selected from diesters of maleic acid.

17. The method of claim 1, wherein the diester is selected from C1-4 alkyl diesters of maleic acid, or mixtures thereof.

18. The method of claim 1, wherein the diester is diethyl maleate.

19. A polyaspartic ester composition made by the method of claim 1.

* * * * *